(12) United States Patent
Hubschman et al.

(10) Patent No.: US 8,945,140 B2
(45) Date of Patent: Feb. 3, 2015

(54) SURGICAL PROCEDURES USING INSTRUMENT TO BOUNDARY SPACING INFORMATION EXTRACTED FROM REAL-TIME DIAGNOSTIC SCAN DATA

(75) Inventors: Jean-Pierre Hubschman, Beverly Hills, CA (US); Steven Schwartz, Los Angeles, CA (US); Jason T. Wilson, Los Angeles, CA (US); Tsu-Chin Tsao, Manhattan Beach, CA (US); James S. Gibson, Manhattan Beach, CA (US)

(73) Assignee: Vantage Surgical Systems, Inc., Irvine, CA (US)

(*) Notice: Subject to any disclaimer, the term of this patent is extended or adjusted under 35 U.S.C. 154(b) by 100 days.

(21) Appl. No.: 13/169,076

(22) Filed: Jun. 27, 2011

(65) Prior Publication Data

US 2012/0022546 A1 Jan. 26, 2012

Related U.S. Application Data

(63) Continuation-in-part of application No. 13/164,671, filed on Jun. 20, 2011.

(60) Provisional application No. 61/358,793, filed on Jun. 25, 2010, provisional application No. 61/356,150, filed on Jun. 18, 2010.

(51) Int. Cl.
*A61B 17/3205* (2006.01)
*A61F 9/007* (2006.01)
*A61B 19/00* (2006.01)

(52) U.S. Cl.
CPC .......... *A61F 9/00736* (2013.01); *A61B 19/5244* (2013.01); *A61B 19/2203* (2013.01); *A61B 2019/5214* (2013.01);

(Continued)

(58) Field of Classification Search
USPC .................................. 606/166, 107; 600/587
See application file for complete search history.

(56) References Cited

U.S. PATENT DOCUMENTS 5,836,882 A * 11/1998 Frazin ........................... 600/462
6,299,591 B1 * 10/2001 Banko ............................ 604/22

(Continued)

OTHER PUBLICATIONS

Andrew I. Comport, et al., "Real-Time Markerless Tracking for Augmented Reality: The Virtual Visual Servoing Framework," IEEE Transactions on Visualization and Computer Graphics, vol. 12, No. 4, Jul./Aug. 2006, pp. 615-628.

*Primary Examiner* — Thomas McEvoy
*Assistant Examiner* — Julie A Szpira
(74) *Attorney, Agent, or Firm* — Andres F. Arrubla; Victor Siber

(57) ABSTRACT

The present disclosure is directed to improved phacoemulsification procedures involving the use of processed non-visual three-dimensional data (i.e. diagnostic scan data) to provide a surgeon with additional guidance concerning the distance separating a working end of a phacoemulsification instrument and the posterior capsule of the eye during a surgical procedure involving the removal of the crystalline lens of an eye. Such information is implemented to aid the surgeon in cutting or scoring the lens to a desired depth while minimizing the risk of penetrating the posterior portion of the capsule with the working end of the instrument. Some embodiments provide for the visual and/or auditory conveyance of distance information to the surgeon. Additional embodiments can provide for overlaying visual representations of selected structure information with the images provided to the surgeon.

32 Claims, 8 Drawing Sheets

(52) U.S. Cl.
CPC    *A61B 2019/5234* (2013.01); *A61B 2019/5236* (2013.01); *A61B 2019/5276* (2013.01); *A61B 2019/5291* (2013.01)
USPC .......................................... 606/107; 606/166

(56)  References Cited

U.S. PATENT DOCUMENTS

| | | |
|---|---|---|
| 7,428,318 B1 | 9/2008 | Madsen et al. |
| 2004/0002653 A1* | 1/2004 | Greppi et al. ................. 600/439 |
| 2004/0199171 A1* | 10/2004 | Akahoshi ...................... 606/107 |
| 2005/0190972 A1 | 9/2005 | Thomas et al. |
| 2007/0073309 A1* | 3/2007 | Kadziauskas et al. ........ 606/107 |
| 2007/0191862 A1* | 8/2007 | Ellis .............................. 606/107 |
| 2009/0306581 A1* | 12/2009 | Claus .............................. 604/22 |
| 2010/0312252 A1* | 12/2010 | Jia et al. ........................ 606/107 |
| 2012/0007839 A1 | 1/2012 | Tsao et al. |
| 2012/0022408 A1* | 1/2012 | Hubschman et al. ......... 600/587 |
| 2012/0184846 A1* | 7/2012 | Izatt et al. ..................... 600/425 |

* cited by examiner

SURGICAL PROCEDURES USING INSTRUMENT TO BOUNDARY SPACING INFORMATION EXTRACTED FROM REAL-TIME DIAGNOSTIC SCAN DATA

RELATED APPLICATIONS

This application claims the benefit of U.S. Provisional Patent Application No. 61/358,793, filed Jun. 25, 2010 and is a continuation in part of U.S. patent application Ser. No. 13/164,671 filed Jun. 20, 2011 which in turn claims benefit of U.S. Provisional Patent Application No. 61/356,150 filed Jun. 18, 2010. These applications are incorporated herein by reference as if set forth in full herein.

FIELD OF THE INVENTION

The present invention relates generally to the field of surgical procedures and more particularly to surgical procedures involving nearby boundary regions where surgical instrument penetration is to be minimized or eliminated (i.e. non-fly zones) and wherein computer generated feedback concerning separation distance between a surgical instrument and such boundaries is automatically calculated and optical or auditory feedback is provided to the surgeon to aid in the performance of the surgery. Specific embodiments of the invention relate to the field of ophthalmic surgery and more particularly to the field of phacoemulsification procedures (e.g. cataract removal procedures) wherein diagnostic scan data is processed to supply useful and timely surgical information beyond that which is normally available to a surgeon via visual observation.

BACKGROUND OF THE INVENTION

Surgical procedures: (1) involve certain risks to the patient, (2) take a certain time to perform, (3) take a certain experience or skill level by a surgeon, (4) result in the collateral damage of healthy tissue, (5) result in the excess removal of healthy tissue, (6) result in the inadequate removal of unhealthy tissue, (7) result in the failure to fulfill the surgical goal, (8) require prolonged recovery times, (9) result in extended periods of disability, and/or (10) result in the need for extended therapy. If a surgeon could be provided with more information during the performance of a procedure, be provided with that information in a more timely manner, and/or be provided with that information in a more accessible manner, many such procedures could: (1) be performed with less risk to the patient, (2) be performed more quickly, (3) be performed by a surgeon with less experience or skill, (4) result in reduced collateral damage, (5) result in removal of less healthy tissue, (6) result in more complete removal of unhealthy tissue, (7) result in higher probability of fulfilling the surgical goal, (8) result in less recovery time, (9) result in less disability or shortened periods of disability, and/or (10) result in less need for physical therapy. A need exists in the surgical arts for a method of providing more information, providing this additional information in a timely manner, and/or providing this information in a more accessible manner.

Surgical procedures often involve tissue penetration, manipulation, and/or removal of tissue near a boundary region that is preferably not crossed or damaged by the surgical instrument during the procedure. To avoid inadvertently penetrating such boundaries while still completing the procedure with optimal results may require the procedure to be slowed down while working in these critical areas, require that not all tissue on the working side of the boundary be optimally accessed, or require other procedural complexities to exist. A need exists in the surgical arts for improved procedures and systems for addressing these issues.

In cataract removal procedures, visual observations and surgical experience are used to determine when scoring or cutting the crystalline lens has proceeded to a sufficient depth such that cracking or chopping can be used to break the lens into smaller pieces. Unfortunately, inadequate information can lead to undercutting or overcutting (e.g. including penetration beyond the posterior portion of capsule). A need exists for an improved surgical procedure and system that reduces the risk for posterior capsule damage.

SUMMARY OF THE INVENTION is an object of some embodiments of the invention to provide an improved surgical procedure wherein the provision of more information to the surgeon, the more timely provision of the information, and/or the more accessible provision of the information results in the procedure being performed with less risk to the patient.

It is an object of some embodiments of the invention to provide an improved surgical procedure wherein the provision of more information to the surgeon, the more timely provision of the information, and/or the more accessible provision of the information results in the procedure being performed more quickly It is an object of some embodiments of the invention to provide an improved surgical procedure wherein the provision of more information to the surgeon, the more timely provision of the information, and/or the more accessible provision of the information results in the procedure being successfully performable by a surgeon with less experience or skill, It is an object of some embodiments of the invention to provide an improved surgical procedure wherein the provision of more information to the surgeon, the more timely provision of the information, and/or the more accessible provision of the information results in reduced collateral damage, It is an object of some embodiments of the invention to provide an improved surgical procedure wherein the provision of more information to the surgeon, the more timely provision of the information, and/or the more accessible provision of the information results in the removal of less healthy tissue, It is an object of some embodiments of the invention to provide an improved surgical procedure wherein the provision of more information to the surgeon, the more timely provision of the information, and/or the more accessible provision of the information results the more complete removal of unhealthy tissue, It is an object of some embodiments of the invention to provide an improved surgical procedure wherein the provision of more information to the surgeon, the more timely provision of the information, and/or the more accessible provision of the information results in higher probability of fulfilling the surgical goal, It is an object of some embodiments of the invention to provide an improved surgical procedure wherein the provision of more information to the surgeon, the more timely provision of the information, and/or the more accessible provision of the information results in less recovery time, It is an object of some embodiments of the invention to provide an improved surgical procedure wherein the provision of more information to the surgeon, the more timely provision of the information, and/or the more accessible provision of the information results in less disability or shortened periods of disability.

It is an object of some embodiments of the invention to provide an improved surgical procedure wherein the provision of more information to the surgeon, the more timely provision of the information, and/or the more accessible provision of the information results in less need for physical therapy.

It is an object of some embodiments of the invention to provide an improved method for performing a phacoemulsification procedure.

It is an object of some embodiments of the invention to provide an improved cataract removal procedure.

It is an object of some embodiments of the invention to provide and improved procedure for placing intraocular lenses.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single embodiment or aspect of the invention even though that may be the case with regard to some embodiments or aspects.

A first aspect of the inventions provides a phacoemulsification procedure, including: (a) forming at least one opening in the eye to provide access to the anterior portion of the lens capsule; (b) forming an opening in the anterior region of a lens capsule containing a lens to be removed; (c) inserting a working end of a phacoemulsification instrument through the opening in the anterior region of the lens capsule; (d) obtaining diagnostic scan data for the lens, the posterior portion of the capsule and the working end of the phacoemulsification instrument; (e) analyzing the diagnostic scan data to obtain a separation distance between the working end of the phacoemulsification instrument and the posterior region of the capsule; (f) operating the phacoemulsification instrument while viewing the lens and the working end of the phacoemulsification instrument and while receiving separation distance information from the analysis of the diagnostic scan data and using the separation distance information in the control of the operation of the instrument; wherein during the course of the procedure, the diagnostic scan data, the analysis of the data, and the receiving of the separation distance information are updated a plurality of times.

Numerous variations of the first aspect of the invention exist and, for example, include: (1) the diagnostic scan data is one of (a) OCT data; (b) MRI data, (c) UBM data, and (d) ultrasound data; (2) the viewing of the lens and the working end of the phacoemulsification instrument occurs directly; (3) the viewing of the lens and the working end of the phacoemulsification instrument occurs indirectly (e.g. via an image captured by a camera; (4) the data associated with an entire diagnostic scan being analyzed to identify a location of the working end and a surface of the posterior region of the capsule; (5) only a portion of the data associated with an entire diagnostic scan is analyzed to identify a location of the working end and a relevant portion of posterior region of the capsule; (6) using an image captured by a camera to produce visual image data that is analyzed to at least partially identify a tip location of the working end of the phacoemulsification instrument; (7) identifying the posterior region of the capsule using an intensity gradient based technique; (8) identifying the working end of the phacoemulsification instrument using intensity gradient based techniques; (9) presenting the separation distance information to the surgeon by and auditory signal; (10) presenting separation distance information to the surgeon by a visual signal presented within the image field containing the surgical field of view; (11) updating of captured and displayed visual images occur a plurality of times per second, for example 20 or more times per second or even 100 or more times per second; (12) updating the diagnostic scan data a plurality of times per minute, for example, at a rate of at least once every 10 second, at a rate of at least once per second, or even at a rate of 5 or more times per second; (13) updating the diagnostic scan data upon an indication from the operator; (14) in addition to providing separation distance information, analyzing diagnostic scan data to provide thickness information between an anterior surface of the lens and the posterior portion of the capsule, for example, along lines that are substantially parallel to Z-axis for a plurality of XY locations and wherein in some further variations, the thickness information may be presented as a visual representation to the surgeon overlaid with the visual image being viewed by the surgeon and it may be updated a plurality of times per second (e.g. 20 or more times per second); and (15) in addition to providing separation distance information, analyzing diagnostic scan data and rendering the results of the analysis to proved a visual representation of selected physical structures overlaid with the visual image that is presented to the surgeon.

Additional variations of the fifth variation of first aspect of the invention include having the portion of the data that is analyzed being selected, at least in part, based on a prior known location of the working end of the phacoemulsification instrument. In some such variations the prior known location of the working end of the phacoemulsification instrument includes the location as determined from an immediately preceding analysis. In some such variations the prior known location is used as a central location of a search volume to be analyzed.

Additional variations of the sixth variation of the first aspect of the invention include, for example, (1) using the tip location, at least in part, in defining an analysis region of the diagnostic scan data and/or (2) using the tip location, at least in part, in defining locations to undergo diagnostic scanning.

Additional variations of the first aspect of the invention are possible. In some such variations separation distance may be determined in a variety of different ways, including, for example: (1) identifying the posterior capsule with a plane that is parallel to the XY plane and defining the plane has having a first Z value, determining a second Z-value corresponding to the working end of the instrument, and determining the difference of the first and second Z-values; (2) defining a geometric solid (e.g. a sphere) of a desired but small dimension (e.g. radius) that is centered on the working end of the instrument, and comparing the geometric solid to the identified posterior capsule position to determine if an intersection exists, if not, increase the dimension by a desired incremental resolution step and repeat the intersection comparison, and continue iterations until an intersection is determined whereby a separation distance is determined to have a value somewhere between the immediately preceding dimension and the dimension that resulted in intersection; and (3) create progressively offset capsule surface representations, where each offset representation has an incremental step size, until the working end is intersected and then use the count of the number of steps and their respective spacings, with or without taking into consideration the last step, to determine the separation distance; (4) assuming that the posterior portion of the capsule has a relatively planar central region which defines an XY plane from which a Z-axis extends toward the more anterior portions of the eye, and wherein the gap is measured as a distance between the working end and the capsule along a line that is substantially parallel to the Z-axis; (5).

Further variations of the ninth variation of the first aspect of the invention include using an auditory signal or signals selected from one or more of: (1) a series of discrete pulse-like signals that can vary in temporal duration based on a predetermined set of distance ranges; (2) a series of discrete pulse-like signals that can vary in temporal separation based on a predetermined set of distance ranges; (3) a signal whose pitch varies in frequency based on a predetermined set of distance ranges; and (4) a signal that enunciates different sounds, selected from the group consisting of numbers, letters, words, or phrases based on a predetermined set of distance ranges.

Further variations of the tenth variation of the first aspect of the invention include using a visual signal or signals selected from one or more of: (1) color variations overlaid on the working end of the phacoemulsification instrument based on a predetermined set of distance ranges; (2) a geometric shape (e.g. a circular or elliptical image) centered on the working end of the phacoemulsification instrument based on a predetermined set of distance ranges; (3) a shape located in proximity to the working end of the phacoemulsification instrument selected from the group consisting of numbers, letters, words, phrases, or geometric shapes based on a predetermined set of distance ranges; (4) a color in combination with a shape located in proximity to the working end of the phacoemulsification instrument selected from the group consisting of numbers, letters, words, phrases, or geometric shapes based on a predetermined set of distance ranges; (5) a tinting of a selected portion of the image within the field of view based on a predetermined set of distance ranges; (6) a shape located within the field of view selected from the group consisting of numbers, letters, words, phrases, or geometric shapes based on a predetermined set of distance ranges; and (7) an intensity modulation of a portion of the visual signal within a field of view based on a predetermined set of distance ranges; and (8) the overlaid visual representation and visual image are aligned with one another using markerless tracking methods. Other variations may, for example, present an auditory signal or signals in addition to the visual signal or signals which may, for example, include one or more of the further variations of the ninth variation of the first aspect of the invention as noted above.

A second aspect of the invention provides a medical procedure for penetrating, or removing target tissue, to a desired thickness from a posterior or distal boundary of the target tissue without penetrating the boundary with a working end of a surgical instrument, the procedure comprising: (a) forming at least one opening in a covering tissue in proximity to the anterior surface of the target tissue to provide access to said anterior surface of the target tissue; (b) inserting a working end of surgical instrument through the opening in the cover tissue to contact the target tissue; (d) obtaining diagnostic scan data for the target tissue, the posterior boundary, and the working end of the surgical instrument; (e) analyzing the diagnostic scan data to obtain a separation distance between the working end of the surgical instrument and the posterior boundary region; (f) operating the surgical instrument while viewing the target tissue, the working end of the surgical instrument and while receiving separation distance information from the analysis of the diagnostic scan data and using the separation distance information in controlling or deciding how to control of the surgical instrument; wherein during the course of the procedure, the diagnostic scan data, the analysis of the data, and the receiving of the separation distance information are updated a plurality of times.

A third aspect of the invention provides a diagnostic or therapeutic medical procedure involving the penetration or removal of target tissue from one or more selected target tissue locations or placement of a material at one or more selected locations relative to a posterior or distal boundary of the target tissue without penetrating the boundary with a working end of surgical instrument, the procedure including: (a) inserting a working end of an instrument into the target tissue; (b) obtaining diagnostic scan data for the target tissue, the posterior boundary, and the working end of the instrument; (c) analyzing the diagnostic scan data to obtain a separation distance between the working end of the surgical instrument and the posterior boundary region; and (d) moving and operating the instrument while viewing the target tissue, the working end of the instrument, and while receiving separation distance information from the analysis of the diagnostic scan data and using the separation distance information in controlling or deciding how to control of the movement and operating of the instrument; wherein during the course of the procedure, the diagnostic scan data, the analysis of the data, and the receiving of the separation distance information are updated a plurality of times.

Numerous variations of the second and third aspects of invention exist. Some such variations provide surgical instruments selected from the group consisting of (1) a needle, (2) a probe, (3) forceps, (4) a clamp, (5) scissors, (6) a knife, (7) a spreader, (8) a retractor, (9) tweezers, (10) an delivery cannula, (11) an aspirating cannula, (12) a cystotome, (13) a hydrodissector, (14) a hook, (15) a phaco chopper (16) a polisher, (17) a scrapper, (18) a tissue extraction tool, and (19) a deposition tool. Other variations provide the features noted in many of the variations of the first aspect of the invention, mutatis mutandis.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

Figure 2A:
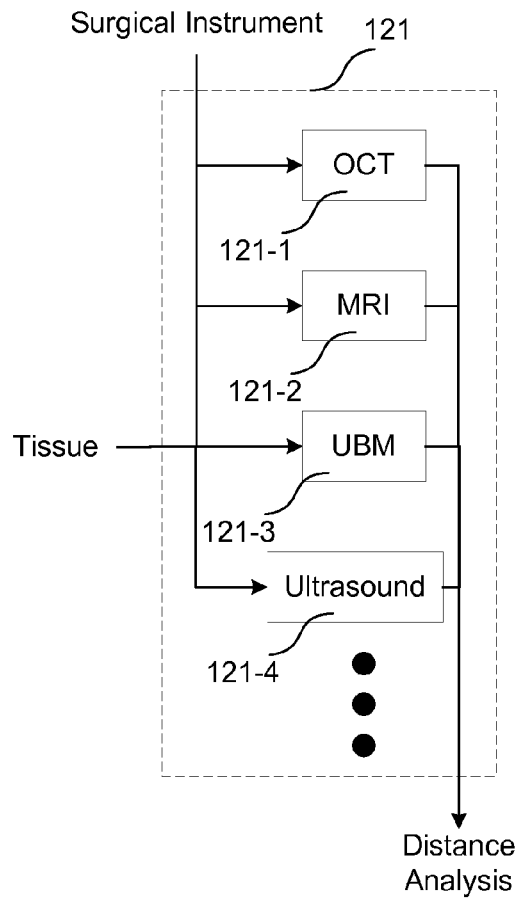
Figure 2C:
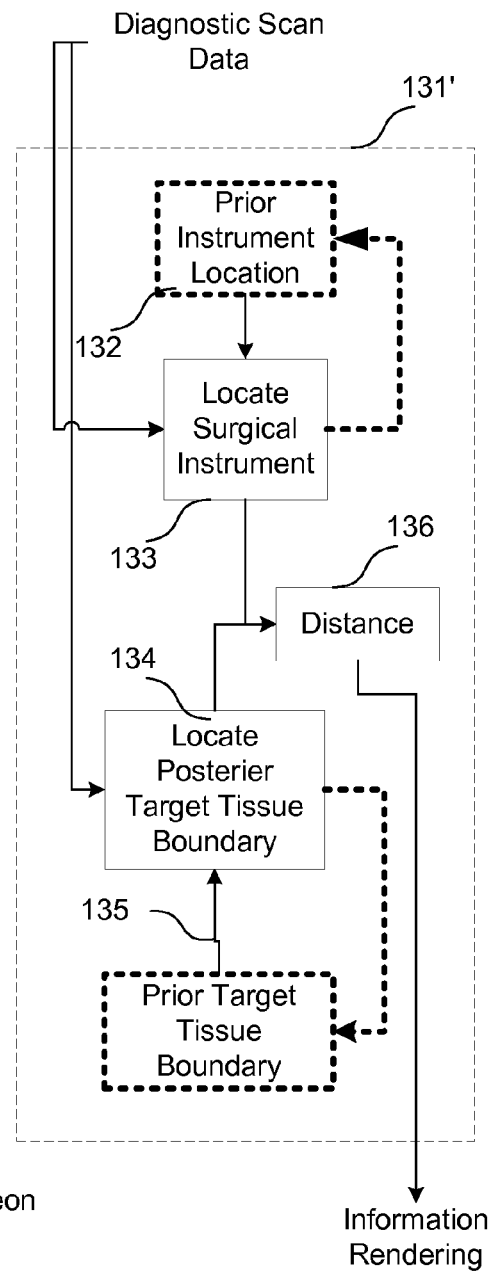

Numerous variations of the first embodiment are possible. Some of those possibilities are set forth in FIGS. 2A-2C which provide examples of various alternatives that may form part of the procedure of the first embodiment, such as alternative diagnostic scan data types (FIG. 2A), rendering alternatives (FIG. 2B), and distance calculations including optional uses of previously known instrument locations (e.g. working end locations that were obtained from previously analyzed diagnostic data) and/or capsule locations (FIG. 2C).

Figure 3:
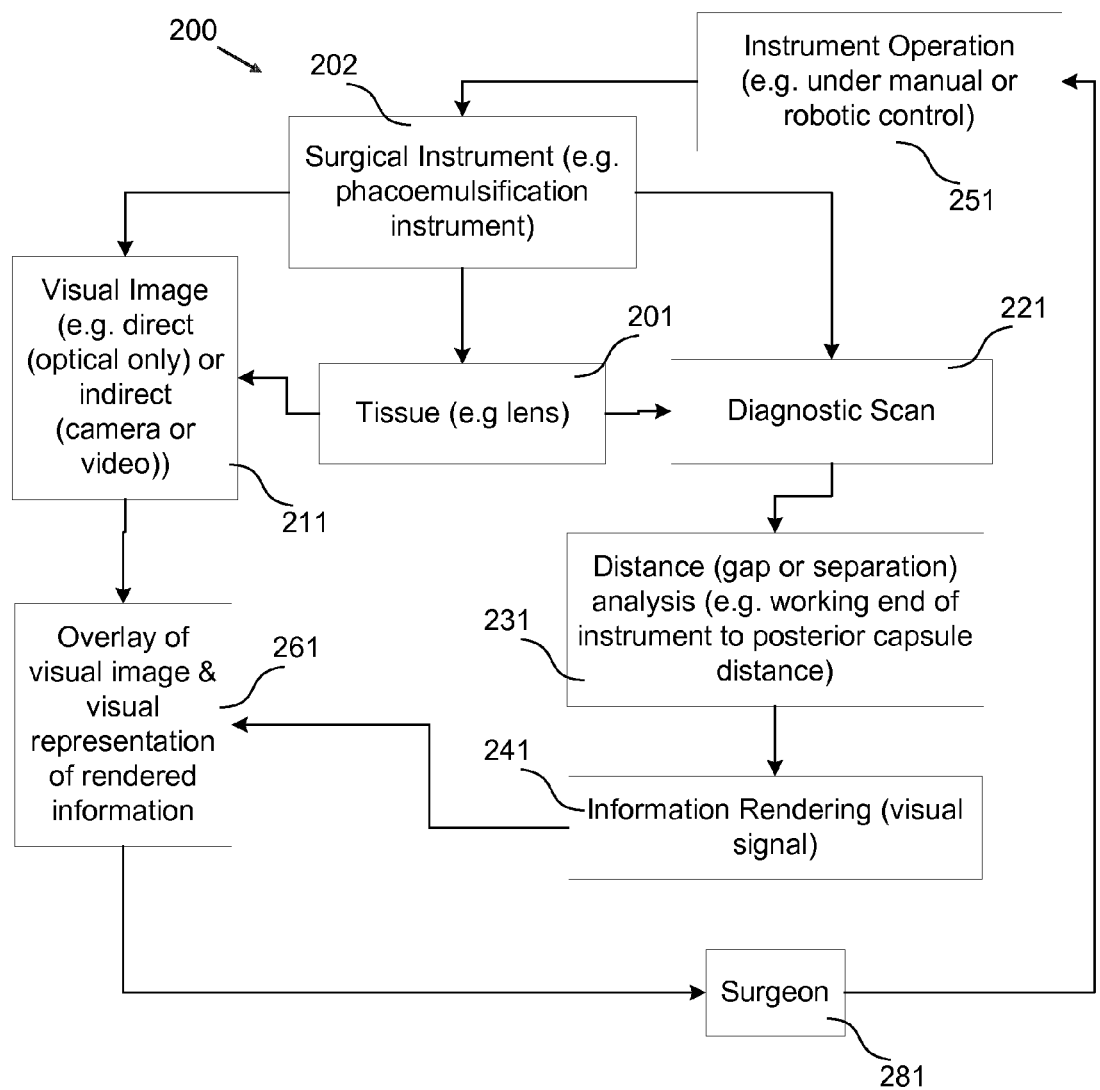

FIG. 3 provides a block diagram representing selected steps of a second embodiment of the invention that is similar to the first embodiment of the invention with the exception that rendered information takes the form of a visual representation that is overlaid with real visual images (e.g. of a surgical region or area) are presented to the surgeon.

Figure 4:
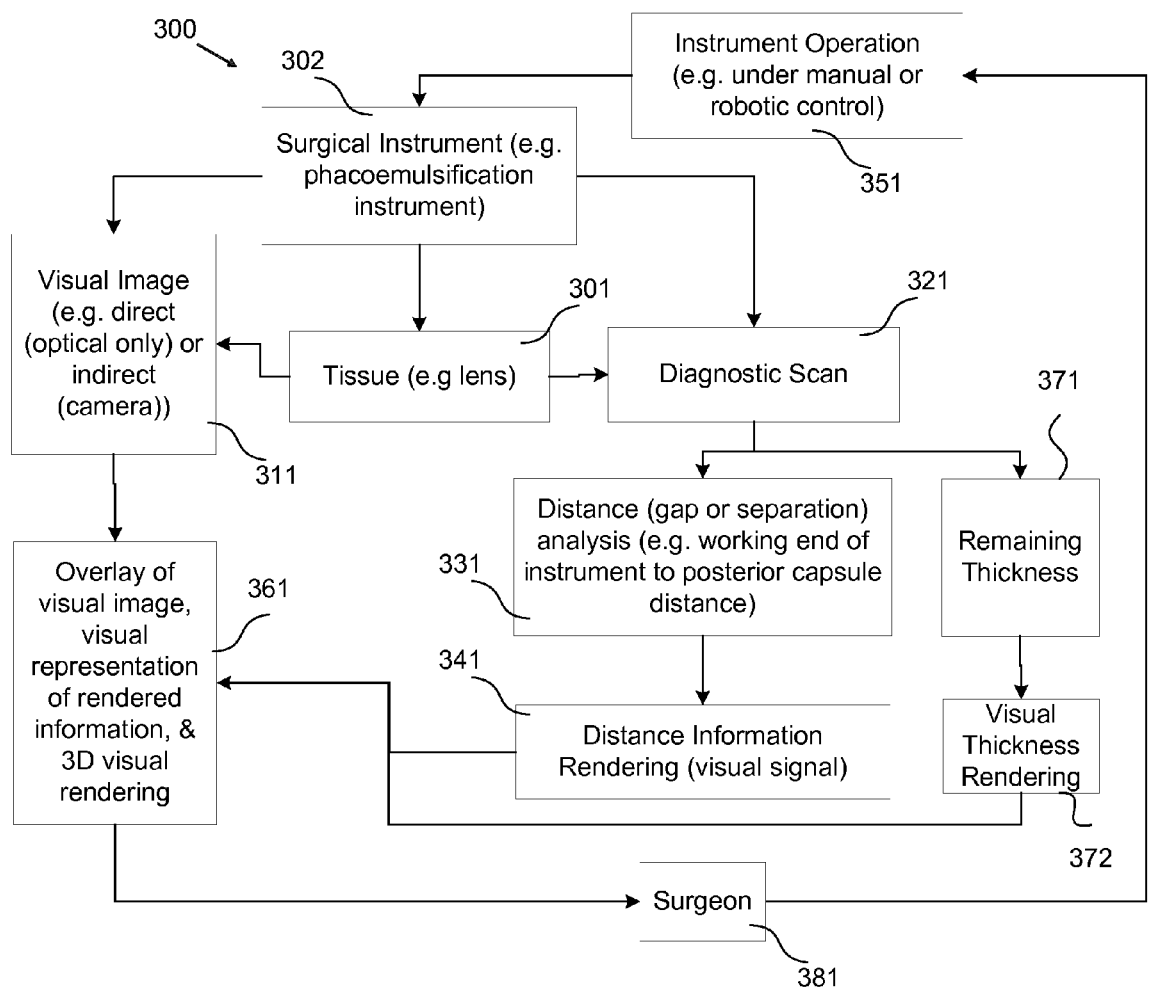

FIG. 4 provides a block diagram representing selected steps of a third embodiment of the invention that is similar to the second embodiment of the invention with the exception that in addition to the diagnostic scan data being used to provide information concerning an instrument to boundary separation distance of a working end of the instrument and the posterior boundary or surface or an allowed fly-zone or penetration zone, the diagnostic scan data is also used to provide information concerning remaining thickness of material that is located between the working end of the instrument and the posterior surface, which thickness may be less than the distance as some of the intervening material may already have been removed, visual information associated with the distance and thickness is then combined with the visual image of the instrument and tissue for presentation to the surgeon.

Figure 5:
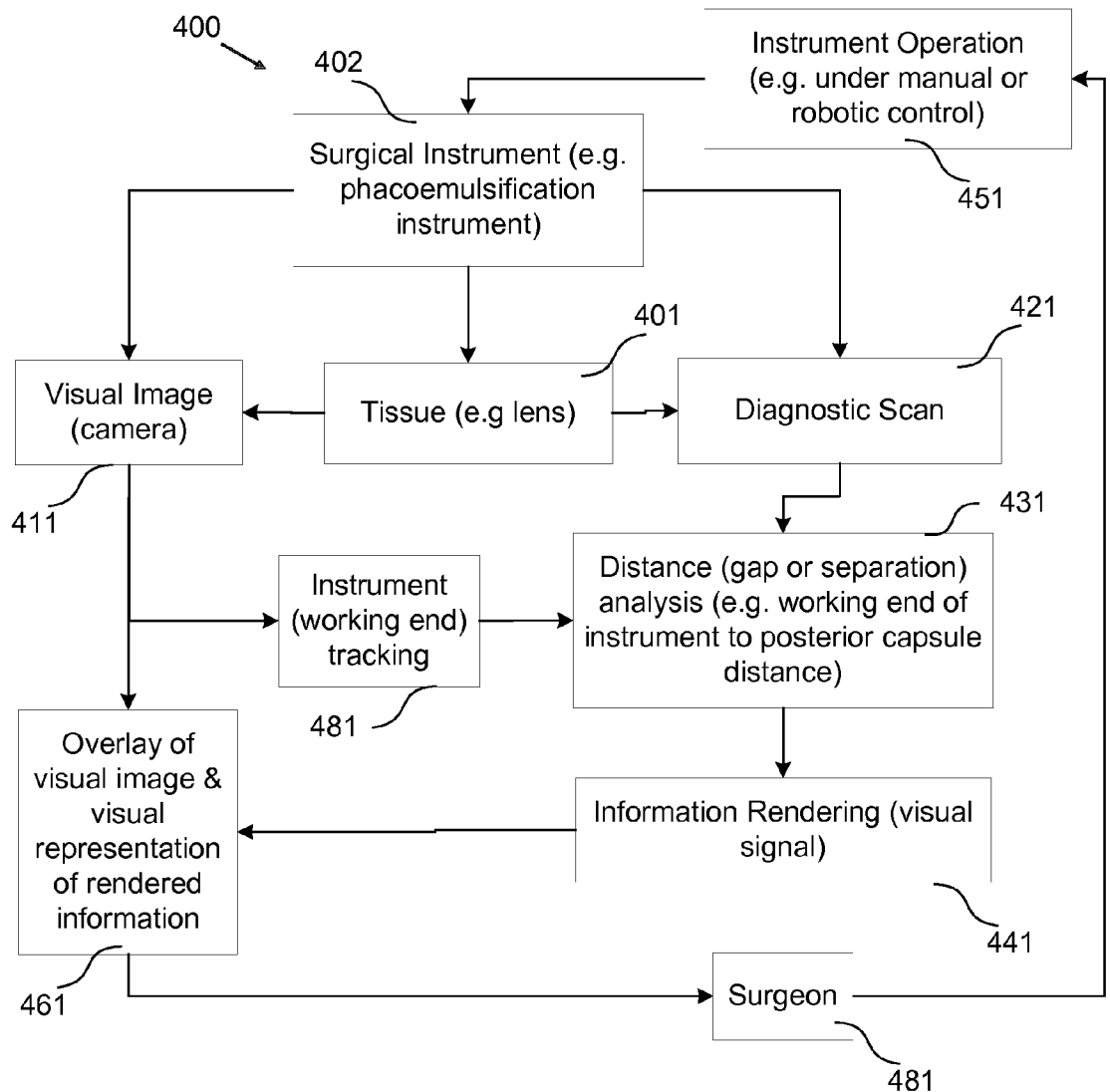

FIG. 5 provides a block diagram representing selected steps of a fourth embodiment of the invention that is similar to the second embodiment of the invention with the exception that the selected information about the position (e.g. location and/or orientation) of the working end of the instrument is tracked and supplied to the distance analysis block to allow improved (e.g. more efficient) analysis by allowing the analysis to be focused on or centered around a known or anticipated position of the working end of the instrument as determined from analysis of the visual image or visual image information (e.g. known or estimated X & Y positioning of the working end may lead to a reduction in the amount of diagnostic data that must be analyzed).

Figure 6:
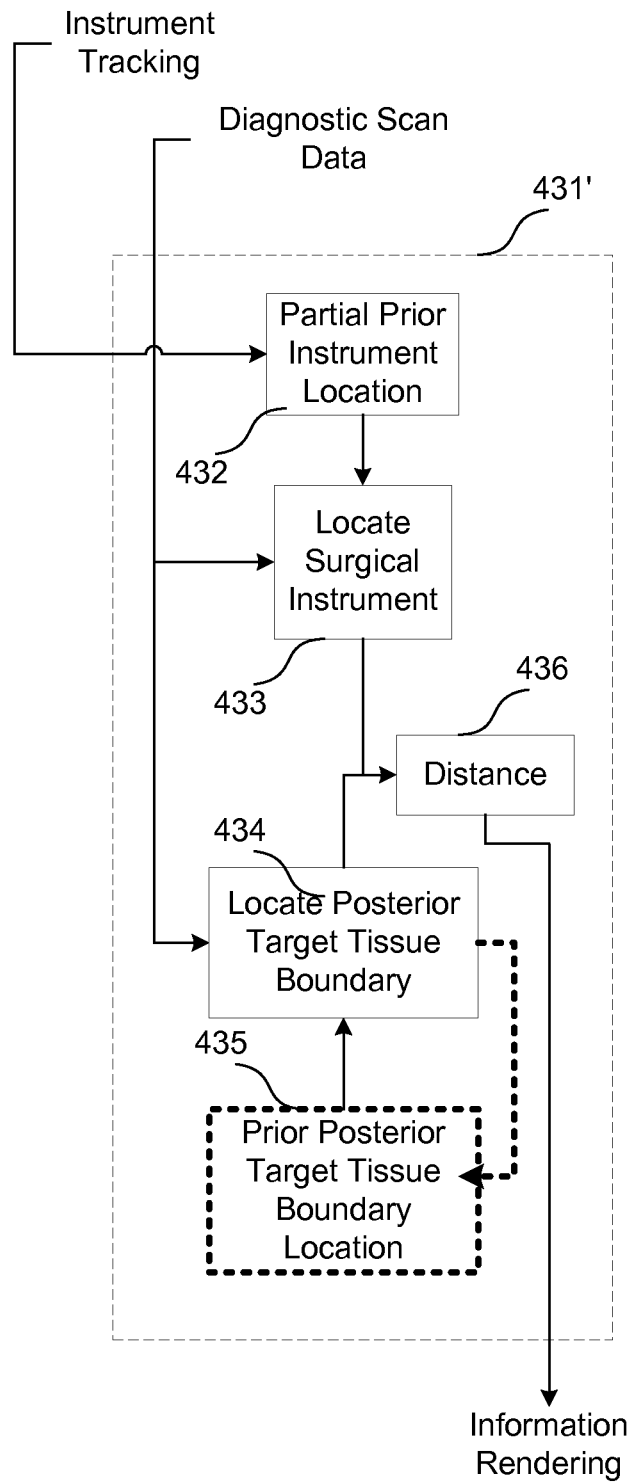

FIG. 6 provides a block diagram of selected substeps that may be involved in the distance analysis process and in particular provides an example of how instrument tracking data of FIG. 5 may be supplied to block 432 as a partial prior instrument location that is used in helping determine a complete current position.

Figure 7:
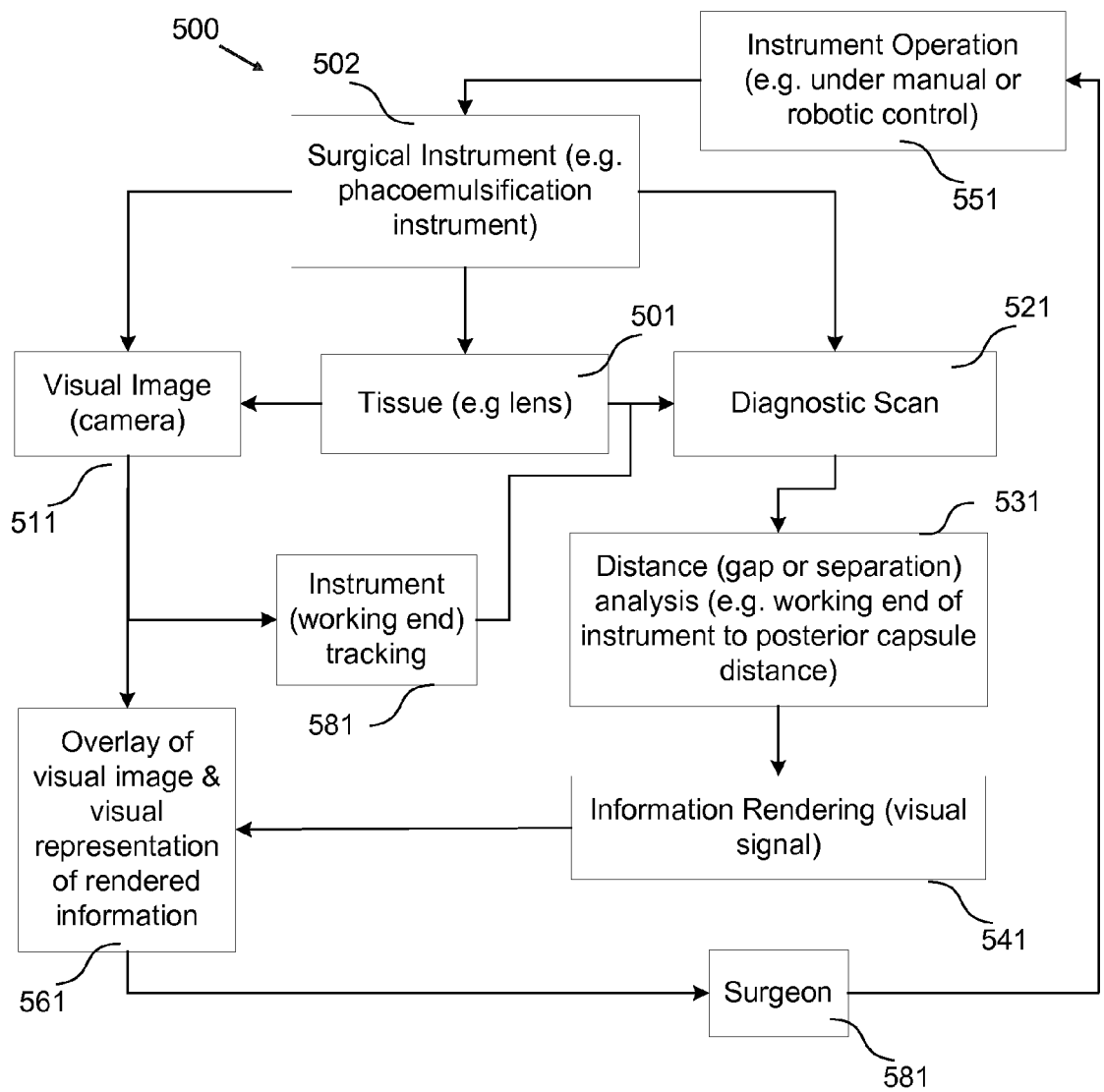

FIG. 7 provides a block diagram representing selected steps of a fifth embodiment of the invention that is similar to the fourth embodiment of the invention with the exception that the instrument tracking information is provided as an input to the diagnostic scan block, as opposed to the distance analysis block so that it may be used in focusing the diagnostic scan to be made on only the selected regions that are necessary to derive the required separation distance information.

Figure 8:
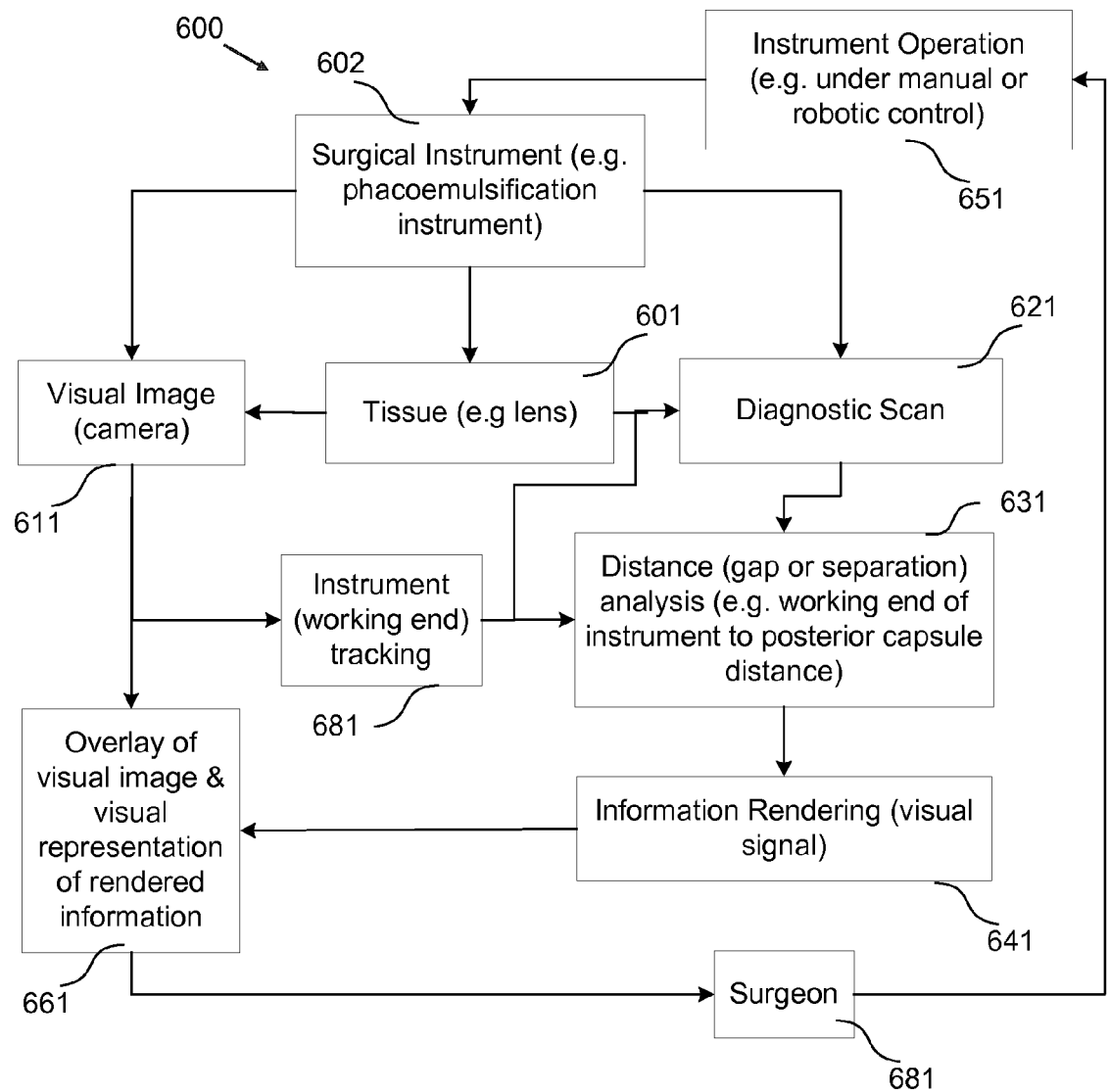

FIG. 8 provides a block diagram representing selected steps of a sixth embodiment of the invention that combines the enhancements of the fourth and fifth embodiments such that tracked position information for the working end is used to both limit the diagnostic scan region and the portion of the diagnostic scan data that will be analyzed to yield the desired separation distance information.

DETAILED DESCRIPTION OF PREFERRED EMBODIMENTS

In some specific and focused embodiments of the invention, a phacoemulsification procedure is provided wherein the surgeon not only uses visual information provided within his/her field of view but also uses instrument tip (i.e. a working end of a phacoemulsification instrument) to posterior capsule spacing (i.e. distance) information that is extracted from three-dimensional diagnostic scan data to aid in determining whether continued cutting or scoring in a given location would risk damaging the capsule. In some embodiments, the distance information is provided in the form of an auditory signal, in others as a visual signal, and in still others as a combination of the two. In some embodiments the visual information is obtained directly (i.e. using only optical elements such as lenses, mirrors, filters, diffraction gratings, apertures, and the like between a source object having a diffuse surface reflection and the eye or eyes of the observer) while in others it is obtained indirectly (i.e. coming from images that were captured by a camera or other image capture device and then displayed).

In other generalized embodiments of the invention, the procedures association with a phacoemulsification process may be applied to other surgical processes, mutatis mutandis. In such generalized embodiments the posterior portion of the capsule is analogous to a no fly-zone that the instrument tip should no penetrate while the crystalline lens is analogous to target tissue that is to be removed or is at least acceptable for penetration. In some such generalized embodiments, the target tissue may be a tumor that is to be removed while the posterior portion of the capsule represents healthy tissue or bounding tissue that is not to be damaged during removal of the tumor.

A generalized phacoemulsification procedure, includes (a) forming at least one opening in the eye to provide access to the anterior portion of the lens capsule; (b) forming an opening in the anterior region of a lens capsule containing a lens to be removed; (c) inserting a working end of a phacoemulsification instrument through the opening in the anterior region of the lens capsule; and (d) operating the phacoemulsification to remove the crystalline lens or to make one or more trenches in the lens so that the lens may be split into one or more smaller pieces which may then be removed.

As used herein, in generalized embodiments, anterior and posterior may, respectively, refer to the front (forward portion) of an organ or body region and the rear (or back) portion of an organ or body region but they may more generally refer to the front or back of a structure based on an access direction with the anterior portion being the portion first accessed while the posterior portion is that portion which requires more penetration to access. When confusion is possible, these terms may be replaced with proximal and distal, respectively.

According to a first specific embodiment of the invention, improvements to step (d) of this generalized procedures of a phacoemulisification process are provided wherein step (d) includes (1) obtaining diagnostic scan data for the lens, the posterior portion of the capsule and the working end of the phacoemulsification instrument; (2) analyzing the diagnostic scan data to obtain a separation distance between the working end of the phacoemulsification instrument and the posterior region of the capsule; and (3) operating the phacoemulsification instrument while directly or indirectly viewing the lens and the working end of the phacoemulsification instrument and while receiving separation distance information resulting from the analysis of the diagnostic scan data and controlling the operation of the instrument based, at least in part, on the separation distance information received, wherein during the course of the operating of the phacoemulsification instrument, the obtaining of diagnostic scan data, the analyzing of the data, and the obtaining of separation distance information occurs a plurality of times.

Figure 1:
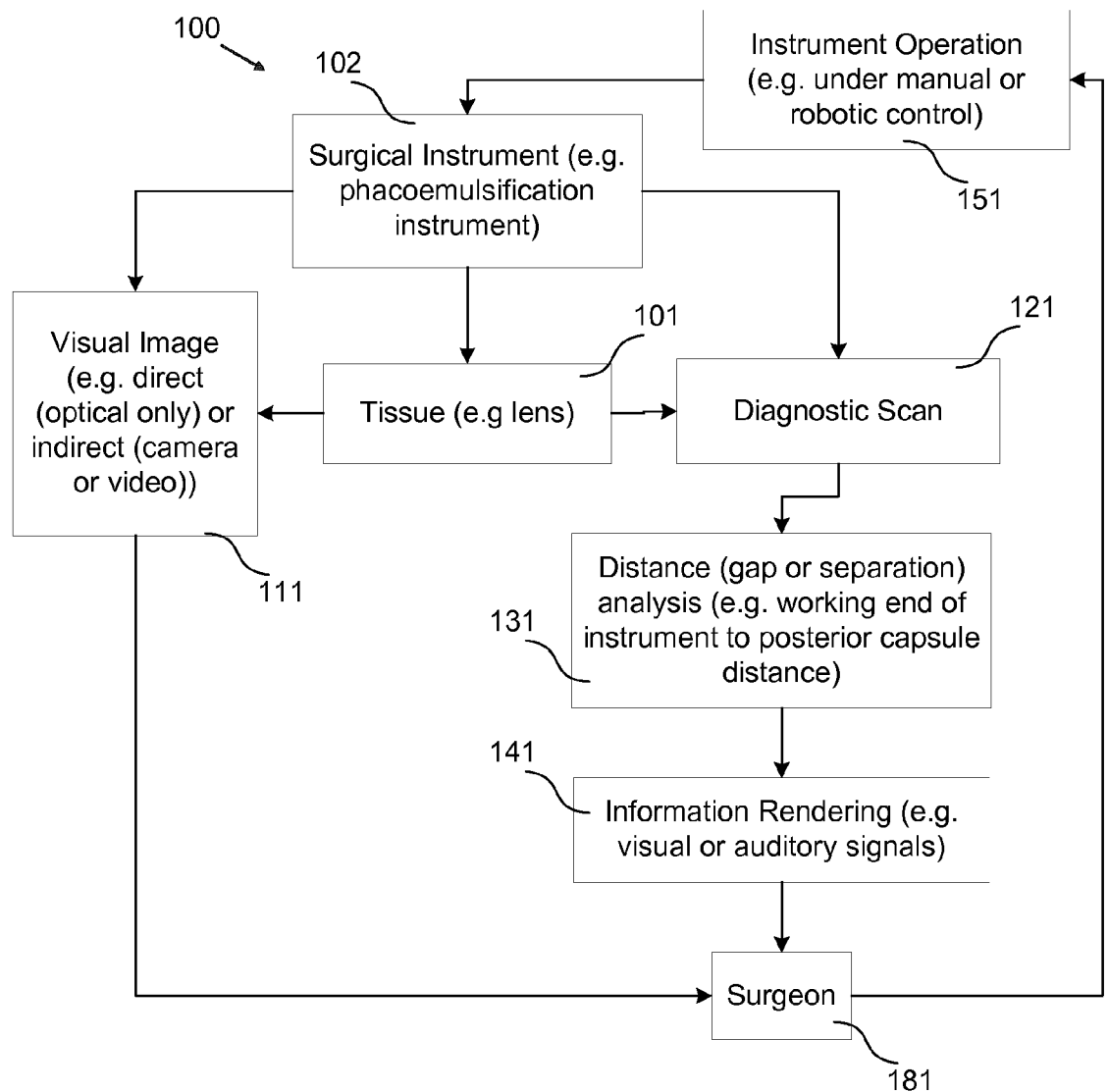
FIG. 1 provides a block diagram representing selected elements of an improved surgical procedure (e.g. an improved phacoemulsification procedure) according to a first embodiment of the invention that focuses on enhancements to using a surgical instrument (e.g. a phacoemulsification instrument) to penetrate or remove tissue (e.g. remove the crystalline lens of the eye) from an anterior surface toward a posterior surface which includes not only the use of visual images of the surgical field of view that is available to the surgeon but also of representations of separation distances of a working end of the surgical instrument (e.g. phacoemulsification instrument) relative to a posterior boundary region defining a non-fly zone (no or limited penetration zone) or posterior portion of tissue to be removed (e.g. relative to an anterior surface of the back wall of the capsule which borders the posterior surface of the lens), wherein the separation distance data is extracted from three-dimensional diagnostic scan data.

FIG. 1 provides a block diagram representing selected elements of an improved surgical procedure (e.g. an improved phacoemulsification procedure) according to a first generalized and specific embodiment of the invention that focuses on enhancements to using a surgical instrument (e.g. a phacoemulsification instrument) to remove tissue (e.g. the crystalline lens of the eye) from an anterior surface toward a posterior surface which includes not only the use of visual images of the surgical field of view that is available to the surgeon but also of representations of separation distances of a working end of the surgical instrument (e.g. phacoemulsification instrument) relative to a posterior boundary or portion of the tissue to be removed (e.g. relative to an anterior surface of the back wall of the capsule which borders the posterior surface of the lens), wherein the separation distance data is extracted from three-dimensional diagnostic scan data.

Element 102 of FIG. 1 calls for (1) a surgical instrument 102 (e.g. phacoemulsification instrument) to be viewed 111, by a surgeon 181, (2) the surgical instrument to interact with tissue 101 which is also subject to viewing 111, and (3) subjecting a combination of the surgical instrument 102 and tissue 101 to a diagnostic scan 121 (e.g. a selected three-dimensional scan). The diagnostic scan information is then analyzed to provide distance information 131 (e.g. distance information between a working end of the instrument and a posterior boundary of the lens tissue, e.g. an anterior surface of the posterior portion of the capsule bounding the lens) and the distance information is rendered 141 into a form appropriate (e.g. visual or auditory) for use by the surgeon. A combination of the visual image 111 of the instrument and tissue with the distance information 141 is then used by the surgeon in further operating the instrument 151 with the process looping back through these information gathering elements/steps to provide updated visual images and distance, i.e. gap or separation, information that keeps the surgeon better informed of a current surgical progress or at least instrument position relative to the tissue so as to minimize inadvertent excessive penetrations of the working end of the instrument beyond a desired boundary region while simultaneously helping ensure that target tissue is at least penetrated to a sufficient or adequate depth into the target tissue to provide an intended surgical result.

Numerous variations of the first embodiment are possible. Some of those possibilities are set forth in FIGS. 2A-2C which provide examples of various alternatives that may form part of the procedure of the first embodiment, such as alternative diagnostic scan data types (FIG. 2A), rendering alternatives (FIG. 2B), and distance calculations including optional uses of previously known instrument locations (e.g. working end locations that were obtained from previously analyzed diagnostic data) and/or capsule locations (FIG. 2C).

Variations of the first embodiment may obtain scan data form a variety sources and may obtain that data in a variety of forms. For example FIG. 2A provides several alternative types of diagnostic scans 121 that may be performed during a given surgery. In different types of surgeries different types of scans may be preferred due to different abilities to distinguish different tissue types, different resolutions available, different scanning speeds, different scanning logistics that are applicability to different surgical circumstances, and the like. In particular, FIG. 2A indicates for example scan types that the used: an OCT scan 121-1, an MRI scan 121-2, a UBM scan 121-3, and/or an ultrasonic scan 121-4. It is understood by those of skill in the art that other scan types may also be used in some alternative embodiments.

Figure 2B:
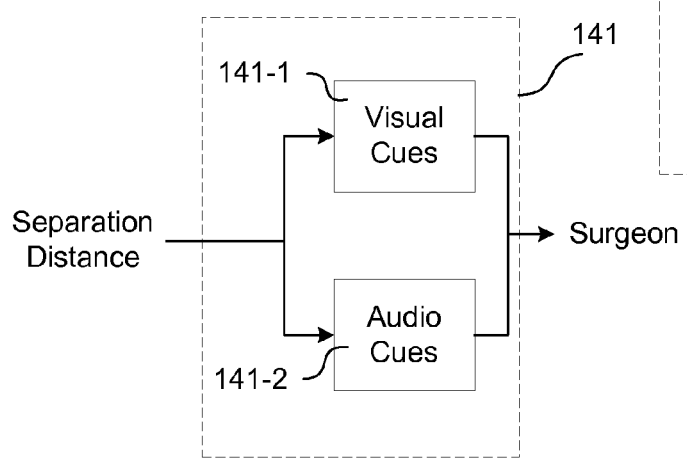

Variations of the first embodiment may provide and/or render distance, information into a variety of forms. FIG. 2B provides two examples of alternative rendering possibilities 141 for separation distance information: (1) visual cues 141-1 and (2) audio cues 141-2. In some embodiments one or the other of these alternatives may be used while in other embodiments both may be used together. Each form of cuing may take on a variety of forms. Examples of visual cues include: (1) a series of discrete pulse-like signals that can vary in temporal duration based on a predetermined set of distance ranges; (2) a series of discrete pulse-like signals that can vary in temporal separation based on a predetermined set of distance ranges; (3) a signal whose pitch varies in frequency based on a predetermined set of distance ranges; and/or (4) a signal that enunciates or provides different sounds, selected from the group consisting of numbers, letters, words, or phrases based on a predetermined set of distance ranges.

Variations of the first embodiment may allow for visual images of the surgical instrument and tissue being operated on to be provided to the surgeon in a variety of different ways. For example visual images may be presented to an eye piece of a microscope and/or provided via display or projection onto an enlarged screen.

Visual cues, associated with the distance information may also be provided in a variety of different ways as well. For example, such cues may be provided as color variations overlaid on the working end of the phacoemulsification instrument based on a predetermined set of distance ranges; as a geometric shape (e.g. a circular or elliptical image) centered on the working end of the phacoemulsification instrument based on a predetermined set of distance ranges; as a shape located in proximity to the working end of the phacoemulsification instrument selected from the group consisting of numbers, letters, words, phrases, or geometric shapes based on a predetermined set of distance ranges; as a color in combination with a shape located in proximity to the working end of the phacoemulsification instrument selected from the group consisting of numbers, letters, words, phrases, or geometric shapes based on a predetermined set of distance ranges; as a tinting of a selected portion of the image within the field of view based on a predetermined set of distance ranges; as a shape located within the field of view selected from the group consisting of numbers, letters, words, phrases, or geometric shapes based on a predetermined set of distance ranges; as an intensity modulation of a portion of the visual signal within a field of view based on a predetermined set of distance ranges; as a flashing signal; and/or as a flashing icon whose size, color, flash rate, or the like may be made to vary with distance. In other embodiment variations, the visual cue may take the form of a separately presented or overlaid 3-D view, 3-D sectional view, a 2-D cut-end view, or 2-D cut side view showing the actual depth of removed material and/or thickness of remaining material along with instrument working end position information, with or without other indications of distance In some embodiment variations, augmented reality techniques, including markerless tracking methods, may be used to display overlaid or composite images containing both a substantially real time image of the surgical area along with enhanced images depicting relevant information extracted from one or more 3-D scans of the surgical region so that enhanced information may be provided to a surgeon. Such augmented reality, image overlaying, and markerless tracking methods are described in a number of the articles and patent applications referenced herein, which are each incorporated herein by reference. The creation of composite images may be done electronically or optically. The creation of composite images may use feedback of actual composite images to provide enhanced or improved overlaying of component images.

Variations of the first embodiment may allow visual image updates to be provided at different rates. For example they may be provided at a rate of several times per second or less or at a rate of 20 times per second or more. Diagnostic scan data may also be updated at different rates. For example they may be updated once every ten seconds or less, at a rate of several times per second or more, or somewhere in between. Alternative diagnostic scan data may be updated upon triggering by an operator/surgeon. In some embodiments, visual image (i.e. surgical area visual images) and diagnostic scan data may be presented at similar refresh rates and synchronized phases with or without an intentional phase shift. In still other embodiments image presentation updates of one image component may be at an integer multiple of the other with or without the slower frequency component image being presented at the same rate as the higher frequency component.

Variations of the first embodiment may allow identification of the posterior boundary region to be made in a variety of different ways. The diagnostic scan data, for example, may be analyzed using intensity gradient based techniques.

Variations of the first embodiment allow for distance analysis to be performed in different ways and scan data to be used in a variety of ways. FIG. 2C provides an example of one such variation wherein a prior surgical instrument location 132 may be used in finding (e.g. focusing a search to find) a current surgical instrument location 133 that may in turn be saved as the prior instrument location 132 for a next determination and is also used, in determining a distance 136 that is the output of block 131' (i.e. a possible variation of Block 131 of FIG. 1). Similarly, a prior location 135 of a posterior boundary (e.g. an anterior surface of a posterior capsule relative to a lens that is the target tissue) may be used in locating (e.g. focusing a search to find) a current position 134 of the posterior boundary, which current position 135 may be used along with the current position 133 of the surgical instrument to determine the distance 136. In some variations, prior location of neither of the surgical instrument location nor the prior location of the boundary will be used to make the distance termination, only the prior location of one of the boundary or the instrument location may be used in finding a current location, or in still other variations both may be used.

FIG. 3 provides a block diagram representing selected steps of a second embodiment of the invention that is similar to the first embodiment of the invention with the exception that rendered information takes the form of a visual representation that is overlaid with real visual images that are presented to the surgeon.

Like elements between FIGS. 1 and 3 are labeled with like reference numerals with the exception that the elements of FIG. 3 use the 200 series while elements in FIG. 1 used the 100 series. Element 241 calls for the rendering to be in visual form which is combined with the visual image 211 of the surgical instrument 202 and tissue 201 before presentation to the surgeon. The combining or overlaying of these visual images may occur optically as described in incorporated U.S. patent application Ser. No. 13/164,671 or electronically while the images remain in a data form. The overlaying may occur using markerless tracking algorithms with or without electronic or optical feedback allowing optimization of image registration. The rendered visual image of the distance data for in a phacoemulsification procedure may take a variety forms such as by identifying the posterior capsule with a plane that is parallel to the XY plane and defining the plane as having a first Z value, determining a second Z-value corresponding to the working end of the instrument, and determining the difference of the first and second Z-values; by defining a geometric solid (e.g. a sphere) of a desired but small dimension (e.g. radius) that is centered on the working end of the instrument, and comparing the geometric solid to the identified posterior capsule position to determine if an intersection exists, if not, increasing the dimension by a desired incremental resolution step and repeating the intersection comparison, and continuing iterations until an intersection is determined whereby a separation distance is determined to have a value somewhere between the immediately preceding dimension and the dimension that resulted in intersection; and/or by creating progressively offset capsule surface representations, where each offset representation has an incremental step size, until the working end is intersected and then use the count of the number of steps and their respective spacings, with or without taking into consideration the last step, to determine the separation distance.

FIG. 4 provides a block diagram representing selected steps of a third embodiment of the invention that is similar to the second embodiment of the invention with the exception that in addition to the diagnostic scan data being used to provide distance information concerning the separation of a working end of the instrument and the posterior surface, the diagnostic scan data is also used to provide information concerning remaining thickness of material that is located between the working end of the instrument and the posterior surface, which thickness may be less than the distance when some of the intervening material has already been removed, visual information associated with the distance and thickness is then combined with the visual image of the instrument and tissue for presentation to the surgeon.

As with FIG. 3 like elements between FIGS. 4 and 3 are identified with like reference numerals with the exception that the reference numerals of FIG. 4 are presented in the 300 series as opposed to the 200 series.

As noted above, in addition to the diagnostic scan data being used to determine distance information 331, the scan data is used to determine remaining thickness as set forth in block 371. This second determination may be made in a variety of different ways. For example it may be based on the scan having sufficient ability to detect not only the instrument tip and the boundary between the target tissue and the anterior surface of an underlying posterior tissue) but also a boundary between an anterior surface of the target tissue that is located below and possibly spaced from the working surface of the instrument. In alternative variations, the thickness may be set to a previously calculated value based on a previously attained and determined distance of the instrument tip from the posterior surface of the target tissue (in the same XY location) that is less than the present distance under the assumptions that the distance is measured in a Z-direction and that any previously attained smaller distance necessarily dictates the previous removal of underlying tissue. The rendered distance information 341 and rendered thickness information 372 are overlaid 361 with the visual image 311. Blocks 341 and 372 may be providing either visual images or data representative such visual images. As noted with regard to FIG. 3 the overlaying may occur optically, electronically, or via a combination of the two (e.g. two images overlaid electronically and the combination overlaid optically with the third or two images overlaid optically, then the combination captured electronically, and subsequently electronically overlaid with the third. As noted with the second embodiment, the overlaying may or may not involve optical or electronic feedback to provide for improved overlaying of the images with success updating of component or composite image frames.

FIG. 5 provides a block diagram representing selected steps of a fourth embodiment of the invention that is similar to the second embodiment of the invention with the exception that the selected information about the position (e.g. location and/or orientation) of the working end of the instrument is tracked and supplied to the distance analysis block to allow improved (e.g. more efficient) analysis by allowing the analysis to be focused on or centered around a known or anticipated position of the working end of the instrument as determined from analysis of the visual image or visual image information (e.g. known or estimated X & Y positioning of the working end may lead to a reduction in the amount of diagnostic data that must be analyzed).

Like elements of FIG. 5 as compared to FIG. 2 are labeled with like reference numeral as those of FIG. 2 with the exception that the elements of FIG. 5 use the 400 series of numerals as opposed to the 200 series. Element 481 is added between element 411 and 431 so that instrument working end information (position and possibly orientation) can be at least partially determined and provided, along with the scan information from 421, to the distance gap analysis block 431 and thereafter the distance information, like in FIG. 2, is rendered per block 441 and provided to block 461 for overlaying. In some embodiment variations, visual image updates will occur more often than diagnostic scan updates. The Instrument working end information associated with block 481 may be derived from the most current visual image presented to block 461 or it may be from visual image information that is relatively current but not necessarily from the most recent visual image update.

FIG. 6 provides a block diagram of selected substeps that may be involved in the distance analysis process and in particular provides an example of how instrument tracking data of FIG. 5 may be supplied to block 432 as a partial prior instrument location that is used in helping determine the complete current position.

In the variation of FIG. 6, surgical instrument tracking information (block 481 of FIG. 5) and diagnostic scan information (block 421 of FIG. 5) are input to block 431', which is an expanded variation of block 431 of FIG. 5, with distance information 436 supplied to the information rendering block 441 of FIG. 5. In the variation of FIG. 6 the instrument tracking information extracted from the visual image information of block 411 is supplied to block 432 as partial prior instrument location information and then passed on to block 433 for determination of surgical instrument location. Diagnostic scan information is provided to block 433 as well so that both inputs may be used in determining the surgical instrument location. The input from block 432 may allow less examination and analysis of the diagnostic scan data to identify the surgical instrument location. Diagnostic scan data is also passed onto block 434 for use in locating the posterior boundary of the target tissue (e.g. anterior surface of the posterior portion of the capsule). Block 434 may also make use of prior saved posterior boundary location information in determining new posterior boundary location and the new posterior boundary location may be saved to the prior boundary location block for subsequent use. The use of prior posterior boundary location information, may allow less examination and analysis of the diagnostic scan data to identify the current posterior boundary location. The new posterior target tissue boundary location from block 434 and surgical instrument location from block 433 are used together to determine a separation distance by block 436 from which the output of block 431' is taken.

FIG. 7 provides a block diagram representing selected steps of a fifth embodiment of the invention that is similar to the fourth embodiment of the invention with the exception that the instrument tracking information is provided as an input to the diagnostic scan block, as opposed to the distance analysis block so that it may be used in focusing the next diagnostic scan onto only the selected regions that are necessary to derive the required separation distance information.

Elements of FIG. 7 that are similar to elements of FIG. 5 are identified with like reference numerals with the exception that reference numerals use the 500 series of numbers. In fact the only real difference between FIGS. 5 and 7 is that the output of block 581 is feed into one of the inputs for block 521 as opposed to block 531. As with the information associated with block 481, the information associated with block 581 may be the most recent visual image information or relatively current information but not the most recent (e.g. it may take longer to perform the diagnostic scan than allowed by the refresh rate of the visual images). The information supplied from block 581 to block 521 may be used to limit the effective diagnostic scan region and thus might aid in reducing scan time associated with gathering the scan data.

FIG. 8 provides a block diagram representing selected steps of a sixth embodiment of the invention that combines the enhancements of the fourth and fifth embodiments such that tracked position information for the working end is used to both limit the diagnostic scan region and the portion of the diagnostic scan data that will be analyzed to yield the desired separation distance information.

Elements of FIG. 8 that are similar to elements of FIGS. 5 and 7 are identified with like reference numerals with the exception that reference numerals use the 600 series of numbers. In fact the only real difference between FIG. 8 relative to FIGS. 5 and 7 is that the output of block 681 is feed into inputs for both block 621 and 631 as opposed to one or the other. As with the information associated with blocks 481 and 581, the information associated with block 681 may be the most recent visual image information or relatively current information but not the most recent (e.g. it may take longer to perform the diagnostic scan than allowed by the refresh rate of the visual images). The information supplied from block 681 to block 621 (as in FIG. 7) may be used to limit the effective diagnostic scan region and thus might aid in reducing scan time associated with gathering the scan data while the information supplied from block 681 to block 631 (as in FIG. 5) may be used to reduce an amount of diagnostic data that must be analyzed to derive the distance information.

Numerous variations of the above noted embodiments are possible. For example, such variations may include modified embodiments resulting from the combination of selected elements from two or more of the six presented specific embodiments. Other modified embodiments can result from combining features of the presented embodiments with selected variations presented above for the aspects of the invention.

Other embodiments may be directed to other medical procedures where selected tissue is to be penetrated or removed (i.e. other than the lens in a phacoemulsification procedure) either to a desired depth below an original anterior or proximal surface or to a desired thickness above a posterior or distal boundary of the target tissue (including to a thickness of zero) and it is desired to determine, know, and make use of current distance information (i.e. between a working end of an instrument and a more posterior boundary region during the tissue removal process such that penetrations of the working end of the instrument beyond the distal boundary are minimized or more preferably do not occur at all). In other alternative embodiment the surgical instrument may be a diagnostic instrument and the procedure may be a diagnostic procedure (e.g. a biopsy procedure). In still other embodiments, the surgical instrument may be a therapeutic or diagnostic instrument that is intended not to necessarily remove significant tissue but to locate a drug, therapeutic material, or diagnostic marker at one or more precise positions relative to a boundary of the target tissue wherein the locating process may involve both visual image observations and correlated distance information for precise placement of the drug, material, or marker. Features of the previously presented embodiments and their variations, as well as features and variations set forth in the aspects of the invention may be combined with the other embodiments presented herein to derive further embodiment variations and alternatives.

In some embodiments, a surgeon may not have direct control over a surgical instrument but instead the surgical instrument may be moved under robotic control based on movements or other signals provided by the surgeon (see blocks 151-651). In such embodiments, another optical or auditory quing to the Surgeon might indicate whether or not a movement of the instrument actually occurred when commanded to make a movement by the surgeon and even whether the instrument movement was in an anticipated movement range.

Further Comments and Conclusions

The methods described herein may be used in combination with the methods set forth in U.S. patent application Ser. No. 13/169,072, by Jean P. HUBSCHMAN et al., filed concurrently herewith, and entitled "Surgical Procedures Using Visual Images Overlaid with Visual Representations of Selected Three-Dimensional Data". Further information about overlaying multiple visual images (whether they be from physical sources or from computer rendered images) can be found in the various patents, patent applications, and non-patent publications referenced herein (e.g. in the '671 application referenced herein above). These referenced patents, applications, and non-patent publications are each incorporated herein by reference as if set forth in full herein.

In some embodiments, three-dimensional data (i.e. data from a diagnostic scan) is processed by a programmed computer to generate a visual representation of the three-dimensional data thereafter the visual representation is positioned and oriented with and overlaid on the image data of the eye so that the visual representation and image data may be viewed simultaneously. In some such embodiments of the invention, the overlaying of the visual representation and image data of the eye occurs via the use of markerless tracking algorithms. Such markerless tracking algorithms are known in the art and have been described previously. See for example the section entitled Markerless Tracking" in U.S. Pat. No. 7,428,318; U.S. Patent Pub. No. 2005-1190972; and Comport et al. IEEE Trans Visual. Compo Graph. 12(4); 615-628 (2006). Additional teachings concerning the overlaying of multiple images can be found in U.S. patent application Ser. No. 13/164,671, filed Jun. 20, 2011 and entitled "Augmented Reality Methods and Systems Including Optical Merging of a Plurality of Component Optical Images". Each of these referenced applications, patents and publications is hereby incorporated herein by reference) as if set forth in full herein.

As used herein surgeon may refer to an actual surgeon or other medical practitioner that is involved in performing a procedure of interest. Diagnostic scan means medical scans that are not simply visible light images of the eye taken with one or more conventional cameras (digital, video, etc.). Visual image means one or more images viewed directly by a surgeon with only optical element extending from the source (e.g. a object with a diffuse reflective surface) or indirectly by a surgeon with an intermediate electronic capture and visual reproduction from electronic data between the surgeon and the source Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. A phacoemulsification procedure, comprising:
   (a) forming at least one opening in the eye to provide access to the anterior portion of the lens capsule;
   (b) forming an opening in the anterior region of a lens capsule;
   (c) inserting a working end of a phacoemulsification instrument through the opening in the anterior portion of the lens capsule;
   (d) obtaining diagnostic scan data for the lens, the posterior portion of the capsule and the working end of the phacoemulsification instrument;
   (e) analyzing the diagnostic scan data associated with the working end of the phacoemulsification instrument to obtain a separation distance between the working end of the phacoemulsification instrument and the posterior portion of the capsule;
   (f) presenting a surgeon with a signal corresponding to the separation distance between the working end of the phacoemulsification instrument and the posterior portion of the capsule; and
   (g) operating the phacoemulsification instrument while receiving the signal corresponding to the separation distance between the working end of the phacoemulsification instrument and the posterior portion of the capsule, wherein the signal presented to the surgeon is updated based on separation distance changes during the operating.

2. The procedure of claim 1 wherein the diagnostic scan data comprises data selected from the group consisting of (1) OCT data; (2) MRI data, (3) UBM data, and (4) ultrasound data.

3. The procedure of claim 1 wherein the presented signal is a visual signal of the lens and the working end of the phacoemulsification instrument which can be viewed directly.

4. The procedure of claim 1 wherein the viewing of the lens and the working end of the phacoemulsification instrument occurs indirectly.

5. The procedure of claim 4 wherein the indirect viewing comprises the viewing of an image captured by a camera.

6. The procedure of claim 1 wherein only a portion of the data associated with an entire diagnostic scan is analyzed to identify a location of the working end and a relevant portion of posterior region of the capsule.

7. The procedure of claim 6 wherein the portion of the data that is analyzed is selected, at least in part, based on a prior known location of the working end of the phacoemulsification instrument.

8. The procedure of claim 7 wherein the prior known location of the working end of the phacoemulsification instrument comprises the location as determined from an immediately preceding analysis.

9. The procedure of claim 8 wherein the prior known location is used as a central location of a search volume to be analyzed.

10. The procedure of claim 5 wherein only a portion of the data associated with an entire diagnostic scan is analyzed to identify a location of the working end and a relevant portion of posterior region of the capsule.

11. The procedure of claim 10 wherein the image captured by the camera produces visual image data that is analyzed to at least partially identify a tip location of the working end of the phacoemulsification instrument.

12. The procedure of claim 11 wherein the tip location is used, at least in part, in defining an analysis region of the diagnostic scan data.

13. The procedure of claim 11 wherein the tip location is used, at least in part, in defining locations to undergo diagnostic scanning.

14. The procedure of claim 1 wherein the posterior region of the capsule is identified using an intensity gradient based technique.

15. The procedure of claim 14 wherein the working end of the phacoemulsification instrument is identified using intensity gradient based techniques.

16. The procedure of claim 1 wherein the separation distance is derived, in part, by a method selected from the group consisting of: (1) identifying the posterior capsule with a plane that is parallel to the XY plane and defining the plane as having a first Z value, determining a second Z-value corresponding to the working end of the instrument, and determining the difference of the first and second Z-values; (2) defining a geometric solid (e.g. a sphere) of a desired but small dimension (e.g. radius) that is centered on the working end of the instrument, and comparing the geometric solid to the identified posterior capsule position to determine if an intersection exists, if not, increase the dimension by a desired incremental resolution step and repeat the intersection comparison, and continue iterations until an intersection is determined whereby a separation distance is determined to have a value somewhere between the immediately preceding dimension and the dimension that resulted in intersection; (3) by creating progressively offset capsule surface representations, where each offset representation has an incremental step size, until the working end is intersected and then use the count of the number of steps and their respective spacings, with or without taking into consideration the last step, to determine the separation distance.

17. The procedure of claim 1 wherein the separation distance information is presented to the surgeon by and auditory signal.

18. The procedure of claim 17 wherein the auditory signal comprises a signal selected from the group consisting of: (1) a series of discrete pulse-like signals that can vary in temporal duration based on a predetermined set of distance ranges; (2) a series of discrete pulse-like signals that can vary in temporal separation based on a predetermined set of distance ranges; (3) a signal whose pitch varies in frequency based on a predetermined set of distance ranges; and (4) a signal that enunciates different sounds, selected from the group consisting of numbers, letters, words, or phrases based on a predetermined set of distance ranges.

19. The procedure of claim 1 wherein the separation distance information is presented to the surgeon by a visual signal presented within the image field containing the surgical field of view.

20. The procedure of claim 19 wherein the visual signal comprises a signal selected from the group consisting of: (1) color variations overlaid on the working end of the phacoemulsification instrument based on a predetermined set of distance ranges; (2) a geometric shape (e.g. a circular or elliptical image) centered on the working end of the phacoemulsification instrument based on a predetermined set of distance ranges; (3) a shape located in proximity to the working end of the phacoemulsification instrument selected from the group consisting of numbers, letters, words, phrases, or geometric shapes based on a predetermined set of distance ranges; (4) a color in combination with a shape located in proximity to the working end of the phacoemulsification instrument selected from the group consisting of numbers, letters, words, phrases, or geometric shapes based on a predetermined set of distance ranges; (5) a tinting of a selected portion of the image within the field of view based on a predetermined set of distance ranges; (6) a shape located within the field of view selected from the group consisting of numbers, letters, words, phrases, or geometric shapes based on a predetermined set of distance ranges; (7) an intensity modulation of a portion of the visual signal within a field of view based on a predetermined set of distance ranges; (8) a flashing signal; and (9) a flashing icon whose size, color, flash rate, or the like may be made to vary with distance.

21. The procedure of claim 20 wherein the separation distance information is additionally presented to the surgeon by and auditory signal.

22. The procedure of claim 21 wherein the auditory signal comprises a signal selected from the group consisting of: (1) a series of discrete pulse-like signals that can vary in temporal duration based on a predetermined set of distance ranges; (2) a series of discrete pulse-like signals that can vary in temporal separation based on a predetermined set of distance ranges; (3) a signal whose pitch varies in frequency based on a predetermined set of distance ranges; and (4) a signal that enunciates different sounds, selected from the group consisting of numbers, letters, words, or phrases based on a predetermined set of distance ranges.

23. The procedure of claim 5 wherein visual images are updated a plurality of times per second.

24. The procedure of claim 23 wherein visual images are updated a rate of at least 20 times per second.

25. The procedure of claim 5 wherein the diagnostic scan data is updated at a rate of at least once every ten seconds.

26. The procedure of claim 25 wherein the diagnostic scan data is updated a rate of at least once per second.

27. The procedure of claim 5 wherein the diagnostic scan data is updated upon receipt of an operator signal.

28. The procedure of claim 1 wherein the posterior portion of the capsule has a relatively planar central region which defines an XY plane from which a Z-axis extends toward the more anterior portions of the eye, and wherein the gap is measured as a distance between the working end and the capsule along a line that is substantially parallel to the Z-axis.

29. A medical procedure for penetrating, or removing target tissue, to a desired thickness from a posterior or distal boundary of the target tissue without penetrating an anterior boundary with a working end of a surgical instrument, the procedure comprising:

(a) forming at least one opening in a covering tissue in proximity to the anterior surface of the target tissue to provide access to said anterior surface of the target tissue;
(b) inserting a working end of surgical instrument through the opening in the cover tissue to contact the target tissue;
(d) obtaining diagnostic scan data for at least one of the target tissue, the anterior boundary and the posterior boundary of the target tissue and the working end of the surgical instrument, wherein the scan data is associated with a location of a physical structure of the surgical instrument in relation to the anterior boundary;
(e) presenting to a surgeon a signal corresponding to the location of a physical structure in relation to the anterior boundary; and
(f) updating the signal while the surgeon moves the surgical instrument.

30. The procedure of claim 29 wherein surgical instrument comprises a instrument selected from the group consisting of (1) a needle, (2) a probe, (3) forceps, (4) a clamp, (5) scissors, (6) a knife, (7) a spreader, (8) a retractor, (9) tweezers, (10) an delivery cannula, (11) an aspirating cannula, (12) a cystotome, (13) a hydrodissector, (14) a hook, (15) a phaco chopper (16) a polisher, (17) a scrapper, (18) a tissue extraction tool, and (19) a deposition tool.

31. A diagnostic or therapeutic medical procedure involving the penetration or removal of target tissue from one or more selected target tissue locations or placement of a material at one or more selected locations relative to a posterior or distal boundary of the target tissue without penetrating the boundary with a working end of surgical instrument, the procedure comprising:
(a) inserting a working end of an instrument into the target tissue;
(b) obtaining diagnostic scan data associated with a location of the working end of the instrument in relation to one or both the target tissue and the posterior boundary from one or more sensors;
(c) presenting to a surgeon a signal correlated to the separation distance between the working end of the surgical instrument and the posterior boundary region; and
(d) updating the signal corresponding to the distance and the surgical instrument is operated.

32. The procedure of claim 31 wherein surgical instrument comprises a instrument selected from the group consisting of (1) a needle, (2) a probe, (3) forceps, (4) a clamp, (5) scissors, (6) a knife, (7) a spreader, (8) a retractor, (9) tweezers, (10) an delivery cannula, (11) an aspirating cannula, (12) a cystotome, (13) a hydrodissector, (14) a hook, (15) a phaco chopper (16) a polisher, (17) a scrapper, (18) a tissue extraction tool, and (19) a deposition tool.

* * * * *